United States Patent [19]

Dyal

[11] 4,059,899

[45] Nov. 29, 1977

[54] METHOD FOR FITTING DENTURES TO VARIOUS JAW POSITIONS

[76] Inventor: John P. Dyal, 408 Coronado Tower, 6006 N. Mesa, El Paso, Tex. 79901

[21] Appl. No.: 625,026

[22] Filed: Oct. 23, 1975

[51] Int. Cl.² ............................................. A61C 13/08
[52] U.S. Cl. ............................................. 32/2; 32/19; 32/32
[58] Field of Search .................................. 32/2, 19, 32

[56] References Cited

U.S. PATENT DOCUMENTS

| | | | |
|---|---|---|---|
| 2,243,377 | 5/1941 | Haller | 32/8 |
| 3,224,096 | 12/1965 | Stuart | 32/32 |
| 3,464,111 | 9/1969 | Gillard | 32/2 |

*Primary Examiner*—Robert Peshock

[57] ABSTRACT

A pair of dentures is prefabricated and placed in a patient's mouth with upper and lower dentures held together in horizontal positions (relative to each other) which conforms to the natural position of the patient's jaw. There, a suitable plastic is set in the denture base to build an anatomical base conforming to the patient's alveolar ridges. The invention encompasses both the equipment and process for properly holding the upper and lower dentures while in the patient's mouth. In one embodiment, a between the dentures positioning device clamps the dentures together in the relative positions of the jaws. In another embodiment, a pair of gear-like racks or tools are attached to the sides of the dentures enabling the proper jaw positioning.

7 Claims, 7 Drawing Figures

A. RETROGNATHIC
B. ORTHOGNATHIC
C. EDGE TO EDGE
D. PROGNATHIC

METHOD FOR FITTING DENTURES TO VARIOUS JAW POSITIONS

This invention relates to apparatus and methods of fitting prefabricated artificial dentures, and more particularly to methods of fitting dentures to conform to a patient's natural jaw position.

Conventional methods of denture fabrication require a high degree of operator skill, sometimes approaching an artistic skill. This requirement has resulted in the use of expensive and time-consuming methods leading to a relatively high cost end product. According to the invention, the operator does not need to have the same high level of artistic skill. Instead, he can utilize the technical help of lesser skilled persons, and the hand labor content or production is reduced during denture fabrication.

In greater detail, until recently, conventional denture fabrication methods have generally required impressions to be taken of the patient's alveolar ridge. Sometimes these impressions were used as a guide to prepare a second and even more custom-made impression. After satisfactory impressions were completed, they were mounted on an articulator for mimicking a denture bite which corresponds to the patient's bite. This adjustment was very important and often required one or more extra fitting steps to check the bite.

After both the impression and the bite are acceptable, the actual construction of the denture begins. First, anatomically shaped base plates are constructed, and then premanufactured teeth are set in wax attached thereto. After the wax-up of the dentures is completed, it is necessary to try them in the patient's mouth. Any number of further adjustments and corrections may or may not be made, as required to obtain a perfect fit. Then, the waxed dentures are invested in plaster within a metal denture flask. The wax is removed and a denture plastic is inserted in the void now present in the flask. After a suitable curing process, usually involving a heat cycle, the flask is opened and the plaster is removed. The processed denture is then cleaned, smoothed, and polished.

The steps described above are somewhat fewer than those which might occur in an actual process. Nevertheless, they are adequate to highlight the painstaking hand labor and the high skill level required to make a conventional set of artificial dentures.

To reduce the cost of artificial dentures and to shorten the time required between the ordering and the delivery of the dentures, prefabricated dentures have been designed, which can be fitted to the patient's mouth during as few as one or two fittings. A completed denture is made on a tray base void of tissue-bearing anatomical form. Then, it is covered wih an impression material that converts the base into a custom-made product which is fitted to the patient's mouth.

Nevertheless, these prefabricated dentures still require considerable time to correct the bite. Sometimes, they set up in an unnatural jaw position so that the patient cannot feel comfortable while wearing the dentures.

Accordingly, an object of the invention is to improve denture fitting so that the lower jaw has a predetermined position, relative to the upper jaw. In this connection, an object is to provide means for fitting prefabricated dentures, with a more functional prosthesis wherein:

a. the lower denture is pre-positioned, relative to the upper denture, in the same horizontally aligned relationship that the patient naturally sets his jaws; and b. the pre-position is firmly held while the fitting is completed.

In keeping with an aspect of the invention, tools or devices are used during the fitting of the prefabricated dentures that will enable the dentist to accurately fit the dentures to the set of the patient's jaw position. In one embodiment, a plurality of devices are provided with upper and lower forms on them that hold the dentures in the horizontally aligned positions, which correspond to most common jaw positions. Hence, the process is one of selecting a proper device and of securing the dentures to it by any suitable means, such as by elastic bands. In another embodiment, gear-like racks are temporarily mounted on each side of both the upper and the lower dentures. By properly matching and meshing the teeth of these racks, the upper and lower dentures may be placed in the horizontal alignment corresponding to the patients's jaw position, and then held together with elastic bands. In both embodiments, the teeth are so held while the anatomical form of the alveolar ridges are set in material lining the dentures.

Two preferred embodiments of the apparatus and examples of the patient's possible jaw sets, may be understood best from a study of the attached drawings wherein.

A number of prefabricated tray dentures are made with teeth already mounted thereon. There are a variety of sizes and shapes of trays so that there is at least one optimum denture for almost any dental arch. The upper and lower tray dentures are correctly measured for the size and shape of the particular dental arches which they will fit. As will become more apparent, the inventive process starts with such artificial dentures and then, the dentist constructs the anatomical form on the tissue-bearing areas while the dentures are held in their desired jaw positions.

These basic jaw positions are determined at birth and remain with the patient throughout life. Therefore, to fit the prefabricated dentures to the patient, this jaw position must be taken into consideration if the dentures are to function at maximum efficiency. Accordingly, professional dentistry requires an analysis of the edentulous patient for fitting of full dentures, in order to determine the relationship of the upper to the lower jaw.

Figure 1:
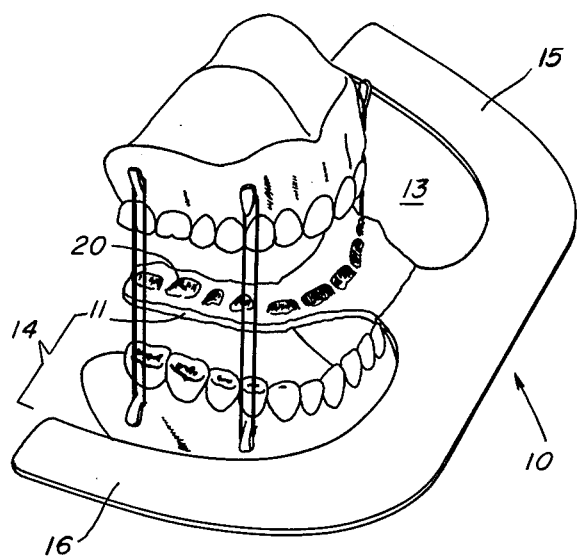
FIG. 1 is a perspective view of a first embodiment using an inter-denture device for giving a prefabricated horizontal alignment set which matches the patient's jaw set.
Figure 2:
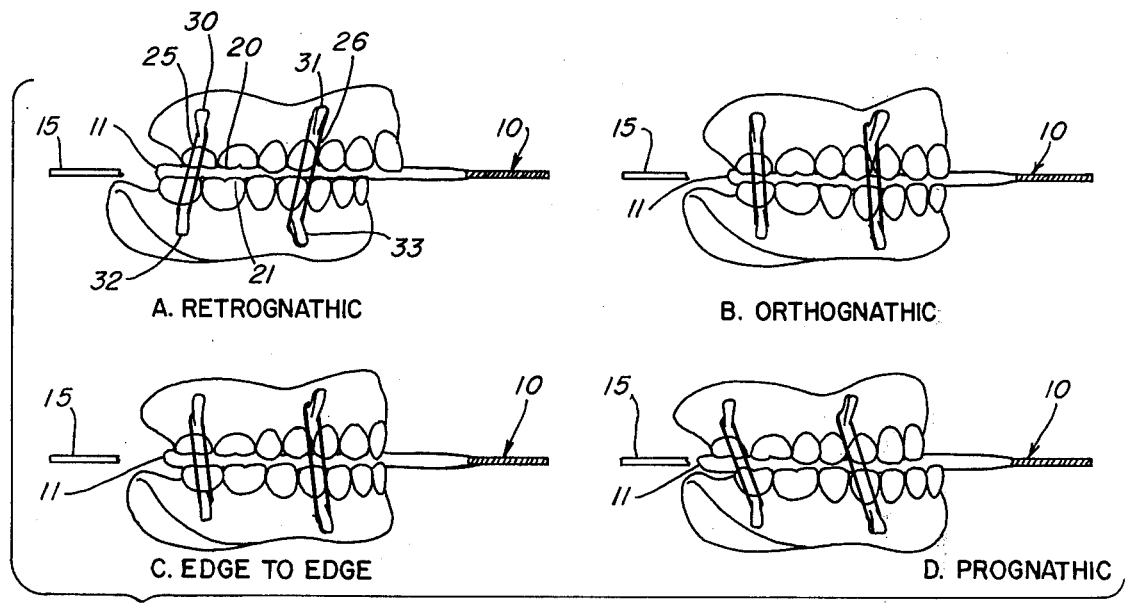
FIGS. 2A-2D are four schematic diagrams explaining the most common jaw positions.

Anatomically speaking, there are four possible relationships between the jaws. That is, the upper jaw may be slightly forward of the lower jaw, and the teeth may have the relationship shown in FIG. 2B. This "ideal" position is known as the "orthognathic" position. However, in many cases the lower jaw assumes other relationships to the upper jaw which are less than "ideal". The lower jaw can be behind the orthognathic position (as shown in FIG. 2A), which results in a more prominent appearance of the upper anterior teeth and is known as a "retrognathic" position. The lower jaw can also be forward so that, when the mouth is closed, the upper and lower teeth assume an "edge-to-edge" relationship as shown in FIG. 2C. When the lower jaw assumes a position anterior to the upper jaw, there is a relationship known as the "prognathic" position (FIG. 2D).

According to the invention, four or more different types of devices 10 are provided. These devices are constructed of any durable material that can be sterilized, such as stainless steel. The device has a central or yoke part 11, which fits into the mouth and between the teeth. On either side of yoke 11, a pair of oppositely disposed cut-outs 13, 14 provide clearance for the patient's cheeks. Outside the clearance spaces 13, 14 are manipulation handles or wings 15, 16 which enable the dentist to move the device (and therefore the dentures) to a desired position.

The top and bottom of the central or yoke part 11 has a series of indentations (as at 20) which coincide with the positions of the teeth, for a patient having the jaw relationship which conforms to yoke part 11. For any device type, the upper and lower indentations 20 are oriented in conformity with any given jaw position, as shown in any one of the FIGS. 2A-2D. For the retrognathic position (FIG. 2A), the upper indentations (as at 20) are far forward of the corresponding lower indentations (as at 21). By inspection of FIGS. 2B-2D, it will be apparent how the upper and lower indentations may be positioned, relative to each other, to accommodate the different jaw positions.

The dentures should be manufactured with flat-plane occlusals on the posterior teeth. If cusps are formed on these posterior teeth, the cusps will prevent opposing teeth from assuming a properly meshed contact position, as the lower denture is moved back or forth to match the correct jaw relationship.

Preferably, the method of the invention, using the device 10, requires the upper denture to be adapted to fit the patient's palatal tissue (by any of several well known means). After the upper denture is fitted to the patient's mouth, the dentist selects the anatomically correct style of device 10 which matches the natural set of the patient's jaws. For example, the device of FIG. 2C is selected for patients having an edge-to-edge bite. Then the upper denture is placed in the upper indentations (as at 20) and the matching lower denture is placed in the lower indentations (as at 21).

The lower denture is attached to the upper denture in any suitable manner, as by elastic bands 25, 26, snapped around opposed tabs 30-33 molded onto the denture gums. The yoke 11 of the positioning device is now between the two dentures.

Next, a tissue adapting material is placed in the lower denture and the whole assembly is inserted in the patient's mouth. The handles or "wings" 15, 16, extending around the face, enable the dentist to determine from external anatomical landmarks when the dentures have assumed the proper position within the mouth.

The patient is then instructed to close his jaws to a predetermined vertical position and to hold that position until the tissue adapting material has set in the lower denture. He then opens his mouth and the assembly is removed. At this time the dentures are removed from the positioning device 10 and the dentures are trimmed and finished for the patient's use. The small tabs 30-33, which hold the elastic bands, are trimmed off and polished until all trace of them disappears from the dentures.

Figure 3:
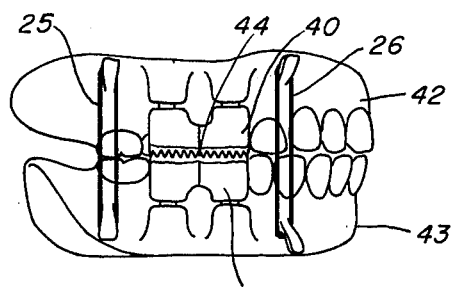
FIG. 3 is a side elevation view of a second embodiment wherein dentures are held together, with a preselected jaw set, by a pair of rack-like gears temporarily attached to each side of the dentures.

FIG. 3 shows a different method of holding the dentures in a desired jaw position. Here a rack or gear-like device 40, 41 is attached to the outside gums of the upper and lower dentures 42, 43, respectively. A longitudinal series of gear teeth 44 is formed on each rack. This way, the lower denture may be moved back or forth to any of the jaw positions (shown in FIG. 2), and at least some of the opposed gear teeth on racks 40, 41 will mesh. Accordingly, the dentures may be placed in almost any horizontally aligned position which matches any selected jaw position. Thereafter, elastic bands 25, 26 may be used to secure the dentures in the selected position.

In utilizing this device, after the upper denture has been fitted, the adapting material is placed in the lower denture. The entire assembly is placed in the patient's mouth, and the patient is instructed to close his mouth to the correct vertical position. When the adapting material has set, he opens his mouth and the dentures are removed. The lugs supporting racks or gears 40, 41 are removed from the dentures, along with the tabs which receive the elastic bands 25, 26. The dentures are trimmed and finished for the patient's use.

For the disclosure of various materials and techniques which may be used to fit and finish the dentures, reference may be made to my U.S. Pat. No. 3,567,806, granted Mar. 2, 1971.

Those who are skilled in the art will readily perceive how changes may be made in the disclosed structure and method. Therefore, the appended claims are to be construed to cover all equivalent structures falling within the true scope and spirit of the invention.

I claim:
1. A method of manufacturing artificial dentures comprising the steps of:
  a. making prefabricated upper and lower dentures with teeth mounted on a tray base;
  b. providing a positioning device having thereon a plurality of preformed indexing means for selectively holding said dentures in a predetermined articulated position according to the natural set of a patient's jaw;
  c. horizontally moving said upper and lower dentures, relative to each other, to a pre-set horizontal position by means of meshing multipositionable racks of gear-like teeth attached to said upper and lower dentures;
  d. attaching together said upper and lower dentures in a selected one of said positions in a pre-set horizontal relationship corresponding to said natural set of said patient's jaw position;
  e. placing a lining of adapting material in said dentures; and
  f. fitting the dentures into a patient's mouth while said dentures are attached together.

2. A denture fitting device comprising a plurality of indexed means each comprising a rigid bite form having index markings preformed on the upper and lower sides thereof for horizontally and simultaneously pre-positioning upper and lower dentures with respect to each other according to any one of many different horizontal relationships of a patient's natural jaw set, depending upon which of said indexing means is used for a given patient, means for resiliently attaching said dentures over said preformed markings in said pre-positioned relationship upon a selected one of said indexed means, and means for simultaneously fitting both said upper and lower dentures to a patient's mouth while said dentures are attached together and to said selected indexed means according to said preformed markings.

3. The device of claim 2 wherein said pre-positioning means comprises a positioning device having a central yoke part corresponding to the relationship of a patient's jaws, said central yoke part being blanked on either side by cut-outs for the patient's cheeks, handle means on the outside of said cheek cut-outs, and means on said central yoke part for fixing the pre-positioned relationship of said dentures.

4. The device of claim 2 wherein said pre-positioning indexing means comprises upper and lower indentations on said central yoke part for receiving the biting edges of the teeth of the upper and lower dentures.

5. A denture fitting device comprising a plurality of indexed means for horizontally pre-positioning upper and lower dentures according to any one of many different horizontal relationships of a patient's natural jaw set, depending upon which of said indexing means is used for a given patient, wherein said pre-positioning indexing means comprises upper and lower indentations on a central yoke part for receiving the biting edges of the teeth of the upper and lower dentures, means for attaching said dentures in said pre-positioned relationship upon a selected one of said indexed means, means for fitting said dentures to a patient's mouth while said dentures are attached together and to said selected indexed means, and tab means on said upper and lower dentures for receiving elastic bands for fastening said dentures together.

6. A denture fitting device comprising a plurality of indexing means for horizontally pre-positioning upper and lower dentures according to any one of many different horizontal relationships of a patient's natural jaw set, depending upon how said indexing means is used for a given patient, said pre-positioning means comprising an opposed pair of racks of gear teeth temporarily attached to said upper and said lower dentures, said racks having many positions which mesh when said dentures are placed in any of the various jaw positions, means for attaching said dentures in said pre-positioned relationship by selectively inter-positioning said racks to form a selected one of said indexed positions, and means for fitting said dentures to a patient's mouth while said dentures are so attached together in said selected indexed position.

7. The device of claim 6 and tab means on said upper and lower dentures for receiving elastic bands for fastening said dentures together.

* * * * *